US007939693B2

(12) United States Patent
Cheng et al.

(10) Patent No.: US 7,939,693 B2
(45) Date of Patent: May 10, 2011

(54) PROCESS FOR PRODUCING SEC-BUTYLBENZENE

(75) Inventors: Jane C. Cheng, Bridgewater, NJ (US); Jihad M. Dakka, Whitehouse Station, NJ (US); Travis A. Reine, Overijse (BE); Jon E. Stanat, Westhampton Beach, NY (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 12/666,333

(22) PCT Filed: Jul. 11, 2008

(86) PCT No.: PCT/EP2008/006073
§ 371 (c)(1),
(2), (4) Date: May 12, 2010

(87) PCT Pub. No.: WO2009/024242
PCT Pub. Date: Feb. 26, 2009

(65) Prior Publication Data
US 2010/0317896 A1 Dec. 16, 2010

Related U.S. Application Data

(60) Provisional application No. 60/957,313, filed on Aug. 22, 2007.

(51) Int. Cl.
*C07C 45/00* (2006.01)
*C07C 37/08* (2006.01)
*C07C 15/067* (2006.01)
(52) U.S. Cl. ........ 568/385; 568/798; 585/446; 585/448; 585/467
(58) Field of Classification Search .................. 568/385, 568/798; 585/446, 448, 467
See application file for complete search history.

(56) References Cited

U.S. PATENT DOCUMENTS

| | | |
|---|---|---|
| 2,584,103 A | 2/1952 | Pines et al. |
| 3,755,194 A | 8/1973 | Avilov et al. |
| 3,819,735 A | 6/1974 | Argento et al. |
| 3,974,095 A | 8/1976 | Volpin et al. |
| 4,051,191 A | 9/1977 | Ward |
| 4,320,242 A | 3/1982 | Onodera et al. |
| 4,329,509 A | 5/1982 | Haag et al. |
| 4,459,426 A | 7/1984 | Inwood et al. |
| 4,468,475 A | 8/1984 | Kuehl |
| 4,490,565 A | 12/1984 | Chang et al. |
| 4,490,566 A | 12/1984 | Chang et al. |
| 4,517,390 A | 5/1985 | Russell et al. |
| 4,891,458 A | 1/1990 | Innes et al. |
| 4,992,606 A | 2/1991 | Kushnerick et al. |
| 5,057,206 A | 10/1991 | Engel et al. |
| 5,059,736 A | 10/1991 | Tamura et al. |
| 5,077,445 A | 12/1991 | Le |
| 5,081,323 A | 1/1992 | Innes et al. |
| 5,149,894 A | 9/1992 | Holtermann et al. |
| 5,177,283 A | 1/1993 | Ward |
| 5,183,945 A | 2/1993 | Stibrany et al. |
| 5,298,667 A | 3/1994 | Iwanaga et al. |
| 5,334,795 A | 8/1994 | Chu et al. |
| 5,336,820 A | 8/1994 | Owen et al. |
| 5,371,310 A | 12/1994 | Bennett et al. |
| 5,476,958 A | 12/1995 | Mautner et al. |
| 5,557,024 A | 9/1996 | Cheng et al. |
| 5,723,710 A | 3/1998 | Gajda et al. |
| 5,779,882 A | 7/1998 | Chester et al. |
| 5,922,920 A | 7/1999 | Bond et al. |
| 6,002,057 A | 12/1999 | Hendriksen et al. |
| 6,051,521 A | 4/2000 | Cheng et al. |
| 6,156,694 A | 12/2000 | Harper |
| 6,169,215 B1 | 1/2001 | Levin et al. |
| 6,169,216 B1 | 1/2001 | Levin et al. |
| 6,297,406 B1 | 10/2001 | Levin et al. |
| 6,313,362 B1 | 11/2001 | Green et al. |
| 6,410,804 B1 | 6/2002 | Levin et al. |
| 6,440,886 B1 | 8/2002 | Gajda et al. |

(Continued)

FOREIGN PATENT DOCUMENTS

EP 0 543 619 5/1993

(Continued)

OTHER PUBLICATIONS

D. Georgiev et al., "Dealkylation of Alkyl-Substituted Aromatic Hydrocarbons in Presence of an Aluminum Silicate Catalyst Communication 1. Kinetics of the Dealkylation of Monoalklbenzenes", Russian Chemical Bulletin, 1959, vol. 8, No. 3, pp. 463-470.
Y. Isakov et al., "Catalytic Properties of Palladium-Zeolite Systems in the Synthesis of Sec-Butylbenzene From Benzene and Ethylene", Inst. Org. Khim, im. N. D. Zelinskogo, Moscow, Russia, Neftekhimiya, 1994, vol. 34, No. 2, pp. 151-170 (Abstract Only; XP002317126).
Y. Isakov et al., "Study of Polyfunctional Zeolite Catalysts. Communication 2. Formation of a Catalyst for Synthesis Off Sec-Butylbenzene Prepared From Nickel Acetylacetonate and CaY Zeolite", Inst. Org. Khim. im. Zelinskogo, Moscow, USSR 1976, vol. 3, pp. 498-504 (Abstract Only).

(Continued)

*Primary Examiner* — Sikarl A Witherspoon
(74) *Attorney, Agent, or Firm* — Jamie Sullivan

(57) ABSTRACT

A process for producing sec-butylbenzene comprises feeding reactants comprising benzene and a $C_4$ olefin to a distillation column reactor having a first reaction zone containing an alkylation catalyst and a second distillation zone, which is located below said first reaction zone and which is substantially free of alkylation catalyst, wherein the ratio of the number of distillation stages in said first reaction zone to the number of distillation stages in said second distillation zone is less than 1:1. Concurrently in the distillation reactor, the reactants are contacted with the alkylation catalyst in the first reaction zone under conditions such that the $C_4$ olefin reacts with the benzene to produce sec-butylbenzene and the sec-butylbenzene is fractioned from the unreacted $C_4$ olefin. The sec-butylbenzene thereby passes as a liquid phase stream from the first reaction zone to the second distillation zone and the liquid phase steam is withdrawn from the distillation column reactor as bottoms.

21 Claims, 1 Drawing Sheet

U.S. PATENT DOCUMENTS

| | | | |
|---|---|---|---|
| 6,717,025 | B1 | 4/2004 | Risch et al. |
| 6,720,462 | B2 | 4/2004 | Kuhnle et al. |
| 6,852,893 | B2 | 2/2005 | Kuhnle et al. |
| 6,911,568 | B1 | 6/2005 | Dandekar et al. |
| 2003/0028060 | A1 | 2/2003 | Dandekar et al. |
| 2003/0083527 | A1 | 5/2003 | Kuhnle et al. |
| 2004/0059167 | A1 | 3/2004 | Clark et al. |
| 2006/0009666 | A1 | 1/2006 | Ramachandran et al. |
| 2006/0178544 | A1 | 8/2006 | Murray et al. |
| 2006/0211901 | A1 | 9/2006 | Boyer et al. |
| 2008/0154082 | A1 | 6/2008 | Dandekar et al. |
| 2009/0306433 | A1 | 12/2009 | Dakka et al. |

FOREIGN PATENT DOCUMENTS

| | | |
|---|---|---|
| EP | 0 578 194 | 1/1994 |
| EP | 1 088 809 | 4/2001 |
| FR | 2 182 802 | 12/1973 |
| GB | 844242 | 8/1960 |
| JP | 2002-282698 | 10/2002 |
| SU | 417405 | 8/1974 |
| SU | 372903 | 10/1974 |
| SU | 265349 | 10/1976 |
| SU | 1245564 | 7/1986 |
| WO | 98/09928 | 3/1998 |
| WO | 02/088051 | 11/2002 |
| WO | 2004/052810 | 6/2004 |
| WO | 2006/015824 | 2/2006 |
| WO | 2006/015826 | 2/2006 |
| WO | 2008/098676 | 8/2008 |

OTHER PUBLICATIONS

K. Minachey et al., "*Alkylation of Benzene by Ethylene on Catalysts Produced From Synthetic Zeolites Ultrasil*", Inst. Org. Khim, im. Zelinskogo, Moscow, USSR, Neftekhimiya, 1988, vol. 28, No. 2, pp. 151-158 (Abstract Only: XP-002317128).

K. Minachev et al., "*Bifunctional Catalysts for the Alkylation of Aromatic Compounds by Ethylene*", USSR, Lektsii-Vses, Shk. Katal, 1981, vol. 2, pp. 76-111 (Abstract Only: XP-002317129).

K. Minachev et al., "*Preparation of Secondary Butylbenzene From Ethylene and Benzene*", IOKh im. Zelinskogo, USSR, Neftepererabotka I Neftekhimiya, Moscow, Russian Federation, 1971, vol. 9, pp. 24-27 (Abstract Only: XP-002317127).

K. Minachev et al., "*Study of the Nature of Bifunctional Catalysts for the Synthesis of Sec-Butylbenzene From Ethylene and Benzene*", Inst. Org. Khim, im. Zelinskogo, Moscow, USSR, Geterog. Katal., $4^{th}$ Edition, 1979, Pt. 2, pp. 485-492 (Abstract Only).

K. Ohkubo et al., "*A Kinetic Study on the Homogeneous Liquid-Phase Oxidation of Cumene in the Presence of Triphenylsulfonium Chloride*", Bull. Chem. Soc., Japan, 1969, vol. 42, No. 7, pp. 1800-1806.

A. Sachanen et al., "*High-Temperature Alkylation of Aromatic Hydrocarbons*", Ind. Eng. Chem., 1941, vol. 33, No. 12, pp. 1540-1544.

R. Sheldon et al., "*Organocatalytic Oxidations Mediated by Nitroxyl Radicals*", Adv. Synth. Catal., 2004, vol. 346, pp. 1051-1071.

V. Sidorov et al., "*Alkylation of Benzene With Olefins*", Sernaya Kislota Protsessakh Neftekhim, 1975, pp. 172-177.

D. Van Sickle et al., "*Liquid-Phase Oxidations of Cyclic Alkenes*", JACS, 1965, vol. 87, No. 21, pp. 4824-4832.

D. Van Sickle et al., "*Oxidations of Acyclic Alkenes*", JACS, 1967, vol. 89, No. 4, pp. 967-977.

Yang, Y-C., "*Phenol*", Supplement B Report No. 22B, Process Economics Program, Stanford Research Institute, Dec. 1977, pp. 113-124 and 261-263.

US 7,939,693 B2

PROCESS FOR PRODUCING SEC-BUTYLBENZENE

CROSS-REFERENCE TO RELATED APPLICATIONS

This application is a National Stage Application of International Application No.
PCT/EP2008/006073 filed Jul. 11, 2008, which claims priority from U.S. Ser. No. 60/957,313 filed Aug. 22, 2007, both of which are incorporated herein by reference.

FIELD

The present invention relates to a process for producing sec-butylbenzene and for converting the sec-butylbenzene to phenol and methyl ethyl ketone.

BACKGROUND

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and coproduces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-124 and 261-263 of Process Economics Report No. 22B entitled "Phenol", published by the Stanford Research Institute in December 1977.

Sec-butylbenzene can be produced by alkylating benzene with n-butenes over an acid catalyst. The chemistry is very similar to ethylbenzene and cumene production. However, as the carbon number of the alkylating agent increases, the number of product isomers also increases. For example, ethylbenzene has one isomer, propylbenzene has two isomers (cumene and n-propylbenzene), but butylbenzene has four isomers (n-, iso-, sec-, and t-butylbenzene). These by-products, especially iso-butylbenzene, have boiling points very close to sec-butylbenzene and hence are difficult to separate from sec-butylbenzene by distillation (see table below).

| Butylbenzene | Boiling Point, ° C. |
|---|---|
| t-Butylbenzene | 169 |
| i-Butylbenzene | 171 |
| s-Butylbenzene | 173 |
| n-Butylbenzene | 183 |

Moreover, isobutylbenzene and tert-butylbenzene are known to be inhibitors to the oxidation of sec-butylbenzene to the corresponding hydroperoxide, a necessary next step for the production of methyl ethyl ketone and phenol. It is therefore important to ensure that the benzene alkylation process is highly selective to sec-butylbenzene rather than the other isomers.

It is also desirable to minimize the production of other by-products such as butene oligomers, dibutylbenzenes and tributylbenzenes. For example, although the polybutylbenzenes can be converted back to the desired sec-butylbenzene by transalkylation, this represents an additional processing cost. The production of butene oligomers raises even more difficult problems. Firstly, they represent an unproductive loss of the butene raw material, and secondly, the $C_{12}$ oligomers are extremely hard to remove from sec-butylbenzene by distillation since their volatility is very close to that of sec-butylbenzene. In addition, any of these oligomers that remain in the sec-butylbenzene alkylate are poisons in the subsequent oxidation step. Thus, any process that produces sec-butylbenzene with reduced amounts of polybutylbenzenes and $C_{12}$ oligomers content is highly advantageous.

In our International Patent Publication No. WO 06/15826 we have described an integrated process for producing phenol and methyl ethyl ketone, in which a feed comprising benzene and a $C_4$ alkylating agent is contacted under liquid phase alkylation conditions with a catalyst comprising zeolite beta or an MCM-22 family molecular sieve to produce an alkylation effluent comprising sec-butylbenzene. The sec-butylbenzene is then oxidized to produce a hydroperoxide and the hydroperoxide is cleaved to produce the desired phenol and methyl ethyl ketone. At least one of the alkylating step, the oxidation step and the cleavage step can be effected by catalytic distillation.

U.S. Patent Application Publication No. 2006/0178544 discloses a method for increasing selectivity of alkylation to monoalkylation comprising: providing a feedstream consisting essentially of alkylating agent and a stoichiometric excess of benzene, the alkylating agent consisting essentially of a molar blend of propylene and one or more linear butene(s); and, contacting the feedstream with a catalytically effective amount of zeolite beta under alkylation reaction conditions which increase selectivity of the alkylation to monoalkylation compared to predicted selectivity to monoalkylation based on the concentration of the alkylating agent and on the molar blend of propylene and one or more linear butene(s). The process may be performed in a fixed bed reactor operating in an upflow or downflow mode or a moving bed reactor operating with concurrent or countercurrent catalyst and hydrocarbon flows. The process may also be performed in a catalytic distillation mode.

U.S. Patent Application Publication No. 2006/0211901 discloses a process for producing cumene and secondary butyl benzene simultaneously in a distillation column reactor by feeding propylene, butylene and benzene to the reactor. Unreacted benzene is removed as overheads and cumene and secondary butyl benzene are removed as products. The catalysts used are acid cation exchange resins or zeolites, particularly beta zeolite.

According to the present invention, it has now been found that when catalytic distillation is applied to the alkylation of benzene with butene, although the competing butene oligomerization reaction also occurs, with proper control of the catalytic distillation process and, in particular of the dimensions of the reaction zone, it is possible to ensure that the sec-butylbenzene and $C_8$ oligomers produced drop quickly from the reaction zone, since they are heavier and less volatile than both benzene and butenes in the reaction zone. Thus the concentration of sec-butylbenzene and $C_8$ oligomers in the reaction zone can be retained at a low level, thereby minimizing their availability for reaction with additional butenes to product polybutylbenzenes and $C_{12}=$oligomers. As a result the catalytic distillation process can be operated so as to produce a sec-butylbenzene alkylate product that contains very low levels of polybutylbenzenes and $C_{12}=$oligomers.

SUMMARY

In one aspect, the invention resides in a process for producing sec-butylbenzene, the process comprising:
(a) feeding reactants comprising benzene and a $C_4$ olefin to a distillation column reactor having a plurality of distillation stages dividing said distillation column reactor into a first reaction zone, which contains an alkylation catalyst, and a second distillation zone, which is located below said first reaction zone and which is substantially free of alkylation catalyst, wherein the ratio of the number of distillation stages in said first reaction zone to the number of distillation stages in said second distillation zone is less than 1:1, and generally less than or equal to 1:2;
(b) concurrently in said distillation column reactor:
(1) contacting said reactants with said alkylation catalyst in said first reaction zone under conditions such that said $C_4$ olefin reacts with said benzene to produce sec-butylbenzene; and
(2) fractionating said sec-butylbenzene from the unreacted $C_4$ olefin, whereby said sec-butylbenzene passes as a liquid phase stream from said first reaction zone to said second distillation zone; and
(c) withdrawing said liquid phase stream from the distillation column reactor as bottoms.

Conveniently, the ratio of the number of distillation stages in said first reaction zone to the number of distillation stages in said second distillation zone is between 1:2 and 1:4, such as between 1:3 and 1:4.

In one embodiment, said distillation column reactor further comprises a third distillation zone, which is located above said first reaction zone and which is substantially free of alkylation catalyst, wherein said third distillation zone comprises a plurality of distillation stages such that the ratio of the number of distillation stages in said first reaction zone to the number of distillation stages in said third distillation zone is less than 1:1, and generally less than or equal to 1:2.

Conveniently, the ratio of the number of distillation stages in said first reaction zone to the number of distillation stages in said third distillation zone is between 1:2 and 1:4, such as between 1:3 and 1:4.

Conveniently, said liquid phase stream contains less than 0.1 wt % of $C_{12}=$oligomers and/or contains less than 1 wt % of polybutylbenzenes.

Conveniently, said conditions in (b) include a temperature between about 30° C. and about 300° C. and/or a pressure between about 200 kPaa and about 1500 kPaa.

Conveniently, said $C_4$ olefin comprises a linear butene, such as 1-butene and/or 2-butene, and typically is contained in a mixed $C_4$ stream.

In one embodiment, said alkylation catalyst comprises zeolite beta or at least one molecular sieve of the MCM-22 family.

In a further aspect, the present invention resides in a process for producing phenol and methyl ethyl ketone, the process comprising:
(a) feeding reactants comprising benzene and a $C_4$ olefin to a distillation column reactor having a plurality of distillation stages dividing said distillation column reactor into a first reaction zone, which contains an alkylation catalyst, and a second distillation zone, which is located below said first reaction zone and which is substantially free of alkylation catalyst, wherein the ratio of the number of distillation stages in said first reaction zone to the number of distillation stages in said second distillation zone is less than 1:1, and generally less than or equal to 1:2;
(b) concurrently in said distillation column reactor:
(1) contacting said reactants with said alkylation catalyst in said first reaction zone under conditions such that said $C_4$ olefin reacts with said benzene to produce sec-butylbenzene; and
(2) fractionating said sec-butylbenzene from the unreacted $C_4$ olefin, whereby said sec-butylbenzene passes as a liquid phase stream from said first reaction zone to said second distillation zone;
(c) withdrawing said liquid phase stream from the distillation column reactor as bottoms;
(d) oxidizing the sec-butylbenzene from said liquid phase stream to produce a hydroperoxide; and
(e) cleaving the hydroperoxide from (d) to produce phenol and methyl ethyl ketone.

DETAILED DESCRIPTION OF THE EMBODIMENTS

Figure 1:
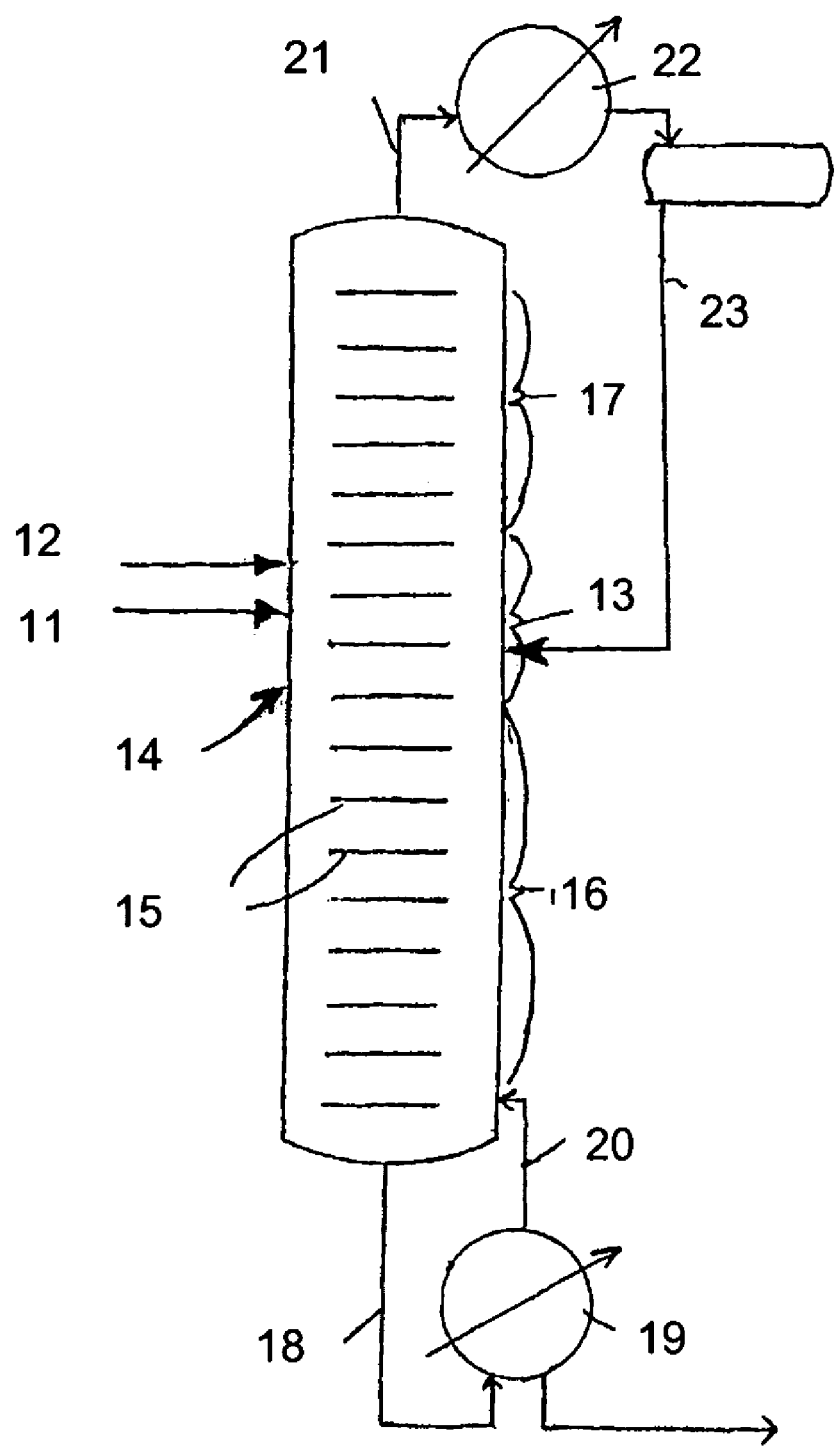
FIG. 1 is a simplified schematic diagram of a process for producing sec-butylbenzene according to one embodiment of the invention.

The present invention is directed to a process for producing sec-butylbenzene and then, in a preferred embodiment, converting the sec-butylbenzene to phenol and methyl ethyl ketone. The conversion takes place in two steps, in which the sec-butylbenzene is initially oxidized to produce the corresponding hydroperoxide and then the resulting hydroperoxide undergoes cleavage to produce the desired phenol and methyl ethyl ketone.

In particular, in the present process the sec-butylbenzene is produced by alkylating benzene with a $C_4$ olefin, such as a mixed butene feed, in a distillation column reactor having a plurality of distillation stages dividing the distillation column reactor into a first reaction zone, which contains an alkylation catalyst, and a second distillation zone, which is located below said first reaction zone and which is substantially free of alkylation catalyst, wherein the ratio of the number of distillation stages in the first reaction zone to the number of distillation stages in the second distillation zone is less than 1:1, and generally less than or equal to 1:2. In this way, the residence time of the sec-butylbenzene and any $C_8$ dimer by-products in the first reaction distillation zone is kept short so that their availability for further reaction with the $C_4$ alkylating agent to produce polybutylbenzenes and $C_{12}=$oligomers is minimized.

In one embodiment, the distillation column reactor further comprises a third distillation zone, which is located above the first reaction zone and which is also substantially free of alkylation catalyst, wherein the third distillation zone comprises a plurality of distillation stages such that the ratio of the number of distillation stages in said first reaction zone to the number of distillation stages in said third distillation zone is less than 1:1, and generally less than or equal to 1:2, such as less than or equal to 1:3. The third distillation zone is useful in keeping the benzene:$C_4$ molar ratio high in the reaction zone.

Benzene Alkylation

The benzene employed in the alkylation step to produce sec-butylbenzene can be any commercially available benzene feed, but preferably the benzene has a purity level of at least 99 wt %.

The alkylating agent can be any olefin, particularly any monoolefin, having 4 carbon atoms and preferably is a linear butene, such as butene-1 and/or butene-2. The alkylating agent can also be an olefinic $C_4$ hydrocarbon mixture such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins; a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table 1 below.

TABLE 1

| Component | Crude $C_4$ stream | Raffinate 1 Solvent Extraction | Raffinate 1 Hydrogn. | Raffinate 2 Solvent Extraction | Raffinate 2 Hydrogn. |
|---|---|---|---|---|---|
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| | |
|---|---|
| Propylene = | 0-2 wt % |
| Propane = | 0-2 wt % |
| Butadiene = | 0-5 wt % |
| Butene-1 = | 5-20 wt % |
| Butene-2 = | 10-50 wt % |
| Isobutene = | 5-25 wt % |
| Iso-butane = | 10-45 wt % |
| N-butane = | 5-25 wt % |

$C_4$ hydrocarbon fractions obtained from the conversion of oxygenates, such as methanol, to lower olefins more typically have the following composition:

| | |
|---|---|
| Propylene = | 0-1 wt % |
| Propane = | 0-0.5 wt % |
| Butadiene = | 0-1 wt % |
| Butene-1 = | 10-40 wt % |
| Butene-2 = | 50-85 wt % |
| Isobutene = | 0-10 wt % |
| N- + iso-butane = | 0-10 wt % |

Any one or any mixture of the above $C_4$ hydrocarbon mixtures can be used in the process of the invention. In addition to linear butenes and butanes, these mixtures typically contain components, such as isobutene and butadiene, which can be deleterious to the process of the invention. For example, the normal alkylation product of isobutene with benzene is tert-butylbenzene which, as previously stated, acts as an inhibitor to the optional subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion processes typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Although not preferred, it is also possible to employ as the alkylating agent in the alkylation step of the invention a mixture of a $C_4$ alkylating agent, as described above, and $C_3$ alkylating agent, such as propylene, so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

Conveniently, the total feed to the alkylation step of the present invention contains on a weight basis (a) less than 1000 ppm, such as less than 500 ppm, for example less than 100 ppm, water; and/or (b) less than 100 ppm, such as less than 30 ppm, for example less than 3 ppm, sulfur; and/or (c) less than 10 ppm, such as less than 1 ppm, for example less than 0.1 ppm, nitrogen.

The alkylation catalyst used in the present process is not critical but generally is elected from zeolite beta or, more preferably, a crystalline molecular sieve having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques, such as using the K-alpha doublet of copper as the incident radiation and a diffractometer equipped with a scintillation counter and associated computer as the collection system.

Materials having the above X-ray diffraction pattern are sometimes referred to as molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

The term "MCM-22 family material" (or "material of the MCM-22 family" or "molecular sieve of the MCM-22 family"), as used herein, includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

The alkylation catalyst can include the molecular sieve in unbound or self-bound form or, alternatively, the molecular sieve can be combined in a conventional manner with an oxide binder, such as alumina, such that the final alkylation catalyst contains, for example, between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic used in the synthesis mixture from remaining in the zeolite crystals as vapor phase crystallization occurs.

The alkylation process is conducted by contacting the organic reactants, i.e., the benzene and the $C_4$ olefin, with the alkylation catalyst under effective alkylation conditions in a first reaction zone of a distillation column reactor comprising a plurality of distillation stages dividing the reactor into the first reaction zone; a second distillation zone, which is located below the first reaction zone and which is substantially free of alkylation catalyst; and preferably a third distillation zone, which is located above the first reaction zone and which is also substantially free of alkylation catalyst. The number of distillation stages in the various zones is arranged so that the ratio of the number of distillation stages in the first reaction zone to the number of distillation stages in the second distillation zone is less than 1:1, generally less than or equal to 1:2 and typically between about 1:2 and about 1:4, whereas the ratio of the number of distillation stages in the first reaction zone to the number of distillation stages in the (optional) third distillation zone is less than 1:1, generally less than or equal to 1:2 and typically between about 1:2 and about 1:4

One embodiment of the alkylation process is shown in FIG. 1, in which a $C_4$ olefin feed 11 and a benzene feed 12 are supplied to a reaction zone 13 of a vertically disposed distillation column reactor 14. The reactor 14 comprises a plurality of vertically spaced distillation trays 15 and is divided into the reaction zone 13, in which each of the trays 15 is loaded with alkylation catalyst, and lower and upper distillation zones 16 and 17, which are located at opposite ends of the reaction zone 13 and in which each of the trays 15 is substantially free of alkylation catalyst. In the embodiment shown the ratio of the number of trays in the reaction zone 13 to the number of trays in the lower distillation zone 16 to the number of trays in the upper distillation zone 17 is about 1:3:2.

The conditions in the reaction zone 13 are maintained such that the $C_4$ olefin feed reacts with the benzene so as to produce sec-butylbenzene and, to a lesser extent, oligomerizes to produce $C_8$ olefins. Since they are heavier and less volatile than the reactants, the sec-butylbenzene and $C_8$ olefins are fractionated from the unreacted benzene and $C_4$ olefin in the reaction zone 13 and form a liquid phase product stream that rapidly falls from the reaction zone 13 and down the lower distillation zone 16 to the lower end of the reactor 14, where the product stream is removed as a bottoms stream 18. The bottoms stream 18 is then passed through a heat exchanger 19, where unreacted benzene is removed and returned to the reactor 14 as recycle stream 20 before the product stream is passed to the optional subsequent oxidation and cleavage steps.

The upper distillation zone 17 serves to continuously remove part of the $C_4$ olefin feed so as keep the benzene:$C_4$ olefin molar ratio high in the reaction zone 13, thereby enhancing the monoselectivity of the alkylation reaction. Any $C_4$ olefin removed in the upper distillation zone 17 escapes the reactor as an overhead vapor stream 21 and is passed through a further heat exchanger 22 before being returned to the reaction zone 13 as recycle stream 23.

Typically, the alkylation conditions include a temperature of from about 30° C. to about 300° C., for example between about 50° C. and about 200° C., and/or a pressure of about 200 kPaa to about 1500 kPaa, for example from about 300 kPaa to about 1000 kPa, and/or a molar ratio of benzene to alkylating agent in the feed from about 1:1 to about 50:1, for example from about 2:1 to about 10:1, and/or a molar ratio of benzene to alkylating agent in the reaction zone of from about 3:1 to about 100:1, for example from about 5:1 to about 20:1.

The present alkylation process is highly selective to sec-butylbenzene and, in particular, it is found that the liquid phase product stream from the distillation column reactor normally contains less contains less than 0.1 wt % of $C_{12}$=oligomers and/or contains less than 1 wt % of polybutylbenzenes. Since the polybutylbenzene content is so low, the alkylation product stream can be fed directly to the optional downstream oxidation and cleavage steps, without removal and transalkylation of the polybutylbenzenes. If desired, however, the alkylation product stream can be distilled to separate the sec-butylbenzene from any polyalkylated products and the polyalkylated products can then be transalkylated with additional benzene to maximize the production of the desired monoalkylated species.

Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite.

Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. The transalkylation reaction is typically conducted under at least partial liquid phase conditions, which suitably may include a temperature of 100 to 300° C., and/or a pressure of 1000 to 7000 kPa, and/or a weight hourly space velocity of 1 to 50 $hr^{-1}$ on total feed, and/or a benzene/polyalkylated benzene weight ratio of 1 to 10.

Sec-Butyl Benzene Oxidation

In order to convert the sec-butylbenzene into phenol and methyl ethyl ketone according to a preferred embodiment, the sec-butylbenzene is initially oxidized to the corresponding hydroperoxide. This may be accomplished by introducing an oxygen-containing gas, such as air, into a liquid phase containing the sec-butylbenzene. The reaction can be performed in the absence of a catalyst but is slow (of the order of <1%/hour at 100 psig (690 kPag) pressure). Improvement in the reaction rate can be achieved by performing the oxidation in the presence of a catalyst, such as a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and/or a pressure of about 0.5 to about 10 atmospheres (50 to 1000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The following Examples are given for illustrative purposes and do not limit the scope of the invention.

EXAMPLE 1

A reactive distillation process for the alkylation of benzene with butene to produce sec-butylbenzene is simulated by means of a computer process simulation using PRO/II from Simsci. To develop this computer simulation of the reactive distillation alkylation scheme, it is necessary to estimate the reaction behavior for both the butene-benzene alkylation and the butene oligomerization. First, the oligomerization reaction is modeled using elementary forward reaction kinetics by comparison to experimental catalytic distillation data of butene oligomerization. The activation energy for each oligomerization reaction is estimated to be 30 kJ/mol (following *App Cat A Gen* 161 (1997) 153-166). Unlike the oligomerization reaction, the alkylation reaction is estimated to be an equilibrium controlled reaction and modeled using the Gibbs Equilibrium Reactor. The selectivity and conversion in the alkylation step are matched to fixed bed experimental data by adjusting the temperature approach to equilibrium and butene component conversion.

The reactive distillation process is simulated by a distillation tower with stripping and rectification sections containing a single reactive zone that is on the 3rd tray from the top (tray3) of a simulated tower having 20 trays. The reactive zone composed of a Gibbs Equilibrium Reactor and a continuous stirred tank reactor (CSTR) is fed by the total liquid flow from tray 3. The Gibbs Reactor performs the alkylation step and the CSTR contains the oligomerization kinetics as previously described. After the reactive zone, the reactor effluent combined with the vapor from tray 4 ($4^{th}$ tray from top) is flashed adiabatically to correctly simulate the vapor and liquid streams from the reactive zone. The liquid is returned to tray 4 below, and the vapor is returned to tray 3 above. The process effectively alkylates the benzene feed with butene in the reactive zone, and any by-product dibutyl alkylate and butene oligomers are fractionated down the column away from the reactive zone.

The simulation is run at a pressure of 70 psig (584 kPa-a), a reaction zone temperature of 150-155° C., a molar ratio of benzene to butene in the feed of 3:1, and a molar ratio of benzene to butene on the reaction tray of 12:1. The conversions and yields from this simulation are shown in Table 2.

TABLE 2

|  | Conversion |
|---|---|
| BENZENE | 32.88% |
| BUTENE-1 | 99.36% |
|  | Selectivity |
| SECBUTYLBENZENE | 97.92% |
| 1,4-DIBUTYLBENZENE | 1.94% |
| C8 OLEFIN DIMER | 0.12% |
| C12 OLEFIN TRIMER | 0.02% |
| Total | 100.00% |

EXAMPLE 2

The simulation of Example 1 is repeated but with 2 reactive trays where the total reaction volume in the 2 reactive trays (model CSTR's) is equivalent to Example 1 and with intermediate flash to simulate staging between reactive trays. The conversions and yields from this simulation are shown in Table 3.

TABLE 3

|  | Conversion |
|---|---|
| BENZENE | 32.85% |
| BUTENE-1 | 99.46% |

TABLE 3-continued

|  | Selectivity |
|---|---|
| SECBUTYLBENZENE | 96.03% |
| 1,4-DIBUTYLBENZENE | 3.80% |
| C8 OLEFIN DIMER | 0.14% |
| C12 OLEFIN TRIMER | 0.03% |
| Total | 100.00% |

It will be seen that the simulation of Example 2 gave a slightly higher C12 olefin yield but almost double the yield of the dibutylbenzene as compared with the simulation of Example 1, demonstrating directionally that increasing the dimensions of the reaction zone increases the level of these impurities in the sec-butylbenzene product.

EXAMPLE 3

A series of simulated reactive distillation processes for the alkylaton of benzene with butene are run in which the distillation tower comprises a single reactive tray positioned between a varying number of upper distillation trays and a varying number of lower distillation trays. Each simulation is run at a pressure of 70 psig (584 kPa-a), a reaction zone temperature of 150-155° C., a molar ratio of benzene to butene in the feed of 3:1, and a butene feed rate of 100 lb-mols/hr. The results obtained are summarized in Table 4 and demonstrate that excellent activity and selectivity to sec-butylbenzene are obtained provided the ratio of the number of reactive trays to the number of lower distillation trays is 1:1 or less. From the point of view of energy utilization, the condenser duty and reboiler duty are least when the ratio of the number of reactive trays to the number of lower distillation trays to the number of upper distillation trays is 1:1:4.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 4

| Case (Top-Rxn-Lower) | Benz Conv | But Conv | SBB Sel | DiBB Sel | C8 Sel | C12 Sel | Condenser Duty MMBTU/hr | Condenser Duty (+) MMBTU/hr | Reboiler Duty MMBTU/hr |
|---|---|---|---|---|---|---|---|---|---|
| 1-1-4 Trays | 32.76% | 99.67% | 97.94% | 1.93% | 0.118% | 0.0169% | −12.066 | 12.066 | 11.575 |
| 2-1-4 Trays | 32.88% | 99.32% | 97.94% | 1.92% | 0.118% | 0.0169% | −12.047 | 12.047 | 11.561 |
| 3-1-4 Trays | 32.93% | 99.17% | 97.94% | 1.93% | 0.118% | 0.0169% | −12.004 | 12.004 | 11.529 |
| 4-1-4 Trays | 32.94% | 99.15% | 97.94% | 1.93% | 0.117% | 0.0169% | −11.971 | 11.971 | 11.503 |
| 4-1-3 Trays | 32.94% | 98.99% | 97.95% | 1.92% | 0.113% | 0.0172% | −12.030 | 12.030 | 11.549 |
| 4-1-2 Trays | 32.94% | 98.20% | 97.96% | 1.91% | 0.110% | 0.0182% | −12.159 | 12.159 | 11.693 |
| 4-1-1 Trays | 32.95% | 95.75% | 98.37% | 1.56% | 0.064% | 0.0086% | −18.065 | 18.065 | 17.636 |

Benz Conv = benzene conversion

But Conv = butene conversion

SBB Sel = sec-butylbenzene selectivity

DiBB Sel = di-butylbenzene selectivity

C8 Sel = C8 olefin oligomer selectivity

C12 Sel = C12 olefin oligomer selectivity

MMBTU/hr = Million British Thermal Units per hour

Top-Rxn-Lower = Top-Reaction-Lower (trays)

The invention claimed is:

1. A process for producing sec-butylbenzene, the process comprising:
    (a) feeding reactants comprising benzene and a $C_4$ olefin to a distillation column reactor having a plurality of distillation stages dividing said distillation column reactor into a first reaction zone, which contains an alkylation catalyst, and a second distillation zone, which is located below said first reaction zone and which is substantially free of alkylation catalyst, wherein the ratio of the number of distillation stages in said first reaction zone to the number of distillation stages in said second distillation zone is less than 1:1;
    (b) concurrently in said distillation column reactor:
        (1) contacting said reactants with said alkylation catalyst in said first reaction zone under conditions such that said $C_4$ olefin reacts with said benzene to produce sec-butylbenzene; and
        (2) fractionating said sec-butylbenzene from the unreacted $C_4$ olefin, whereby said sec-butylbenzene passes as a liquid phase stream from said first reaction zone to said second distillation zone; and
    (c) withdrawing said liquid phase stream from the distillation column reactor as bottoms.

2. The process of claim 1, wherein the ratio of the number of distillation stages in said first reaction zone to the number of distillation stages in said second distillation zone is less than or equal to 1:2, preferably between 1:2 and 1:4.

3. The process of claim 1, wherein said distillation column reactor further comprises a third distillation zone, which is located above said first reaction zone and which is substantially free of alkylation catalyst, wherein said third distillation zone comprises a plurality of distillation stages such that the ratio of the number of distillation stages in said first reaction zone to the number of distillation stages in said third distillation zone is less than 1:1, preferably less than or equal to 1:2, more preferably between 1:2 and 1:4.

4. The process of claim 1, wherein said liquid phase stream contains less than 0.1 wt % of $C_{12}$=oligomers.

5. The process of claim 1, wherein said liquid phase stream contains less than 1 wt % of polybutylbenzenes.

6. The process of claim 1, wherein said conditions in (b) include a temperature between 30° C. and 300° C. and/or a pressure between 200 kPaa and 1500 kPaa.

7. The process of claim 1, wherein said alkylation catalyst comprises zeolite beta or at least one molecular sieve of the MCM-22 family.

8. The process of claim 1, wherein said alkylation catalyst comprises a molecular sieve having an X-ray diffraction pattern including d-spacing maxima at 12.4±0.25, 6.9±0.15, 3.57±0.07 and 3.42±0.07 Angstrom.

9. The process of claim 1, wherein said alkylation catalyst comprises a molecular sieve selected from MCM-22, PSH-3, SSZ-25, ERB-1, ITQ-1, ITQ-2, MCM-36, MCM-49, MCM-56, UZM-8, and mixtures of any two or more thereof.

10. The process of claim 1, wherein said $C_4$ olefin comprises a linear butene.

11. The process of claim 10, wherein said linear butene comprises 1-butene and/or 2-butene.

12. The process of claim 10, wherein said linear butene is contained in a mixed $C_4$ stream.

13. The process of claim 1 and further comprising:
    (d) oxidizing the sec-butylbenzene from said liquid product phase to produce a hydroperoxide; and
    (e) cleaving the hydroperoxide from (d) to produce phenol and methyl ethyl ketone.

14. The process of claim 13, wherein said oxidizing (d) is conducted in the presence of a catalyst, preferably a catalyst selected from:
    (a) an oxo (hydroxo) bridged tetranuclear metal complex comprising manganese;
    (b) an oxo (hydroxo) bridged tetranuclear metal complex having a mixed metal core, one metal of the core being a divalent metal selected from Zn, Cu, Fe, Co, Ni, Mn and mixtures of any two or more thereof and another metal being a trivalent metal selected from In, Fe, Mn, Ga, Al and mixtures of any two or more thereof; and
    (c) an N-hydroxy substituted cyclic imide either alone or in the presence of a free radical initiator.

15. The process of claim 13, wherein the oxidizing (d) is conducted at a temperature of 70° C. to 200° C. and/or a pressure of 50 to 1000 kPa (0.5 to 10 atmospheres).

16. The process of claim 13, wherein the cleaving (e) is conducted in the presence of a homogeneous catalyst.

17. The process of claim 13, wherein the cleaving (e) is conducted in the presence of a homogeneous catalyst comprising at least one of sulfuric acid, perchloric acid, phosphoric acid, hydrochloric acid, p-toluenesulfonic acid, ferric chloride, boron trifluoride, sulfur dioxide and sulfur trioxide.

18. The process of claim 13, wherein the cleaving (e) is conducted in the presence of a heterogeneous catalyst.

19. The process of claim 18, wherein said heterogeneous catalyst comprises a smectite clay.

20. The process of claim 13, wherein the cleaving (e) is conducted at a temperature of 40° C. to 120° C. and/or a pressure of 100 to 1000 kPa and/or a liquid hourly space velocity (LHSV) based on the hydroperoxide of 1 to 50 $hr^{-1}$.

21. A process for producing phenol and methyl ethyl ketone, the process comprising:
    (a) feeding reactants comprising benzene and a $C_4$ olefin to a distillation column reactor having a plurality of distillation stages dividing said distillation column reactor into a first reaction zone, which contains an alkylation catalyst, and a second distillation zone, which is located below said first reaction zone and which is substantially free of alkylation catalyst, wherein the ratio of the number of distillation stages in said first reaction zone to the number of distillation stages in said second distillation zone is less than 1:1;
    (b) concurrently in said distillation column reactor:
        (1) contacting said reactants with said alkylation catalyst in said first reaction zone under conditions such that said $C_4$ olefin reacts with said benzene to produce sec-butylbenzene; and
        (2) fractionating said sec-butylbenzene from the unreacted $C_4$ olefin, whereby said sec-butylbenzene passes as a liquid phase stream from said first reaction zone to said second distillation zone;
    (c) withdrawing said liquid phase stream from the distillation column reactor as bottoms;
    (d) oxidizing the sec-butylbenzene from said liquid product phase to produce a hydroperoxide; and
    (e) cleaving the hydroperoxide from (d) to produce phenol and methyl ethyl ketone.

* * * * *